(12) United States Patent
Konoike et al.

(10) Patent No.: US 12,252,510 B2
(45) Date of Patent: Mar. 18, 2025

(54) METHOD FOR PURIFYING ANTIBODY OR ANTIBODY-LIKE MOLECULE

(71) Applicant: KANEKA CORPORATION, Osaka (JP)

(72) Inventors: Fuminori Konoike, Takasago (JP); Kazunobu Minakuchi, Takasago (JP)

(73) Assignee: KANEKA CORPORATION, Osaka (JP)

( * ) Notice: Subject to any disclaimer, the term of this patent is extended or adjusted under 35 U.S.C. 154(b) by 1027 days.

(21) Appl. No.: 17/268,637

(22) PCT Filed: Aug. 23, 2019

(86) PCT No.: PCT/JP2019/033086
§ 371 (c)(1),
(2) Date: Feb. 16, 2021

(87) PCT Pub. No.: WO2020/045290
PCT Pub. Date: Mar. 5, 2020

(65) Prior Publication Data
US 2021/0198309 A1 Jul. 1, 2021

(30) Foreign Application Priority Data
Aug. 31, 2018 (JP) .................................. 2018-163228

(51) Int. Cl.
*C07K 1/34* (2006.01)
*C07K 1/02* (2006.01)
*C07K 16/00* (2006.01)

(52) U.S. Cl.
CPC .................. *C07K 1/34* (2013.01); *C07K 1/02* (2013.01); *C07K 16/00* (2013.01)

(58) Field of Classification Search
CPC . C07K 1/34; C07K 1/02; C07K 16/00; C07K 16/065; C07K 1/14; C12P 19/30; C12Y 301/30002
(Continued)

(56) References Cited

U.S. PATENT DOCUMENTS

| 2007/0066806 A1 | 3/2007 | Coffman et al. |
| 2010/0145022 A1 | 6/2010 | Romero et al. |

(Continued)

FOREIGN PATENT DOCUMENTS

| JP | 63-275600 A | 11/1988 |
| JP | 2009-508486 A | 3/2009 |

(Continued)

OTHER PUBLICATIONS

US 5,314,993 A, 05/1994, Love et al. (withdrawn)

(Continued)

*Primary Examiner* — Christopher L Chin
*Assistant Examiner* — Christina Lusi
(74) *Attorney, Agent, or Firm* — Birch, Stewart, Kolasch & Birch, LLP

(57) ABSTRACT

The objective of the present invention is to provide a method capable of efficiently removing an impurity from an aqueous solution or a suspension comprising an antibody or an antibody-like molecule and the impurity. The method for purifying an antibody or an antibody-like molecule according to the present invention is characterized in treating an aqueous solution or a suspension comprising the antibody or the antibody-like molecule and an impurity with a water-insoluble inorganic compound, wherein the water-insoluble inorganic compound comprises one or more elements selected from magnesium, calcium and aluminum.

20 Claims, 10 Drawing Sheets

(58) Field of Classification Search
USPC .......................................................... 436/541
See application file for complete search history.

(56) References Cited

U.S. PATENT DOCUMENTS

| | | | |
|---|---|---|---|
| 2019/0211056 A1 | 7/2019 | Ishihara et al. | |
| 2019/0225646 A1* | 7/2019 | Homma | C07K 14/435 |
| 2020/0262866 A1 | 8/2020 | Maks et al. | |
| 2022/0324945 A1* | 10/2022 | Eshima | C07K 1/22 |

FOREIGN PATENT DOCUMENTS

| | | | |
|---|---|---|---|
| JP | 2010-508352 A | | 3/2010 |
| JP | 2013234154 A | * | 11/2013 |
| WO | WO 2017/048391 A2 | | 3/2017 |
| WO | WO 2017/164121 A1 | | 9/2017 |
| WO | WO 2018/043645 A1 | | 3/2018 |
| WO | WO 2018/105982 A1 | | 6/2018 |

OTHER PUBLICATIONS

Rey et al. Fluorine and Health, Chapter 6: Fluoride-Based Bioceramics (2008). Elsevier B.V., First Edition. pp. 296-297. (Year: 2008).*
Stone MT, Kozlov M. Separating proteins with activated carbon. Langmuir. Jul. 15, 2014;30(27):8046-55. doi: 10.1021/la501005s. Epub Jun. 30, 2014. Erratum in: Langmuir. Oct. 7, 2014;30(39):11846. (Year: 2014).*
Mills JB, Mant CT, Hodges RS. One-step purification of a recombinant protein from a whole cell extract by reversed-phase high-performance liquid chromatography. J Chromatogr A. Nov. 10, 2006;1133(1-2):248-53. (Year: 2006).*
Devasahayam, S., Khangoankar, P.R. Particle characteristics of precipitated magnesium carbonate. Mining, Metallurgy & Exploration 12, 157-160 (1995). (Year: 1995).*
Extended European Search Report issued Apr. 25, 2022, in European Patent Application No. 19854100.5.
Chen et al., "Application of calcium phosphate flocculation in high-density cell culture fluid with high product titer of monoclonal antibody", Bioprocess Biosyst. Eng., 2017, vol. 40, pp. 703-714.
Hjelm et al., "Protein A From *Staphylococcus aureus*. Its Isolation By Affinity Chromatography And Its Use As An Immunosorbent For Isolation Of Immunoglobulins", FEBS Letters, 1972, vol. 28, No. 1, pp. 73-76.
International Search Report (PCT/ISA/210) issued in PCT/JP2019/033086 mailed on Nov. 26, 2019.
Kateja et al., "Continuous precipitation of process related impurities from clarified cell culture supernatant using a novel coiled flow inversion reactor (CFIR)", Biotechnology Journal 2016, vol. 11, pp. 1320-1331.
McNerney et al., "BIOT 302: PDADMAC flocculation of CHO cells: A centrifuge-less harvest process for mAb[apos]s", 241st ACS National Meeting&Exposition, 2011, Anaheim, CA. pp. BIOT-302.
Peram et al., "Monoclonal Antibody Purification Using Cationic Polyelectrolytes: An Alternative to Column Chromatography", Biotechnol Prog., 2010, vol. 26, No. 5, pp. 1322-1331.
Riske et al., "The use of chitosan as a flocculant in mammalian cell culture dramatically improves clarification throughput without adversely impacting monoclonal antibody recovery", Journal of Biotechnology, 2007, vol. 128, No. 4, pp. 813-823.
Sommer et al., "Combined polyethylene glycol and $CaCl_2$ precipitation for the capture and purification of recombinant antibodies", Process Biochemistry 2014, vol. 49, pp. 2001-2009.
Written Opinion (PCT/ISA/237) issued in PCT/JP2019/033086 mailed on Nov. 26, 2019.
Zabriskie, et al., "Removal of Nucleic Acid Contaminants Using Nuclease Enzymes during Protein Isolation", Biotechnology and Bioengineering, 1988, vol. 32, No. 1, pp. 100-104.

* cited by examiner

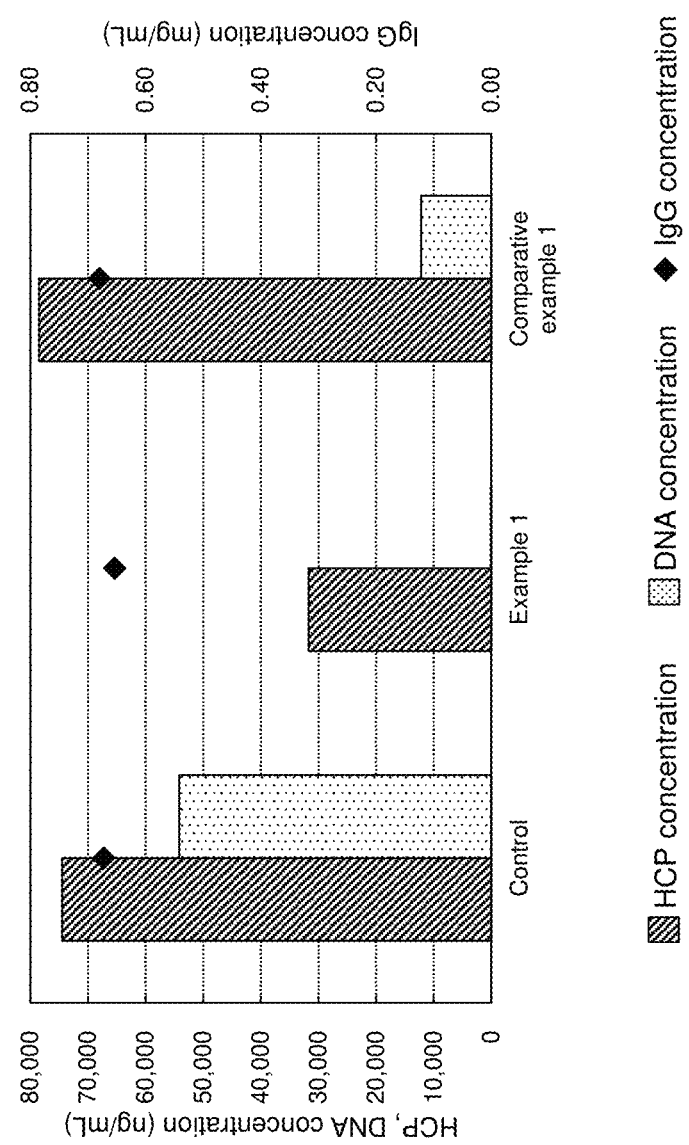
[Fig. 1]

[Fig. 2]
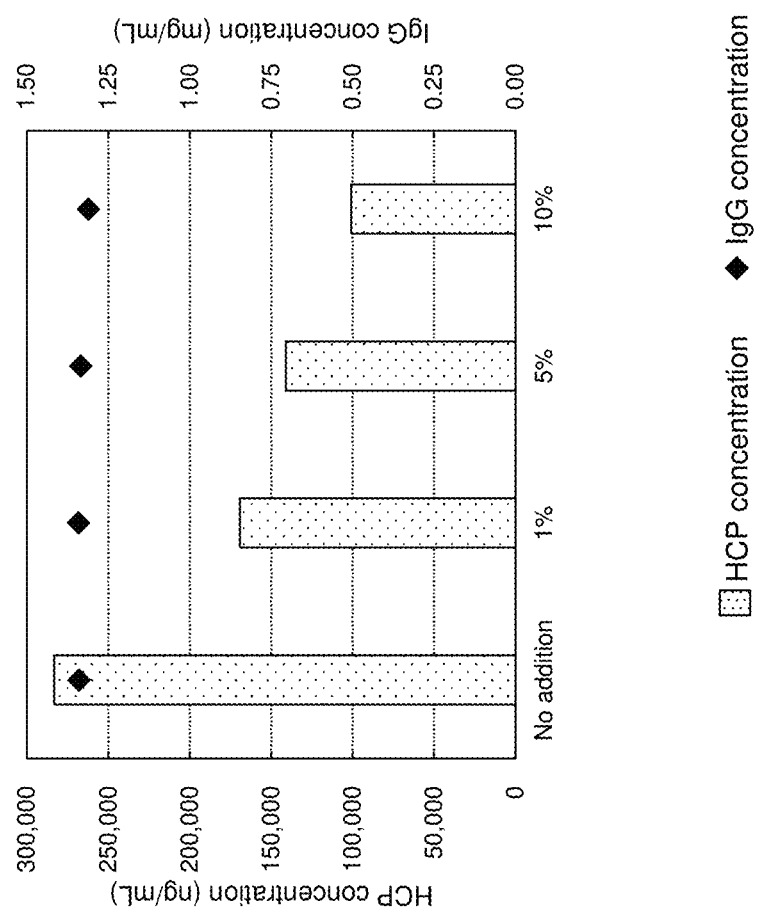

[Fig. 3]
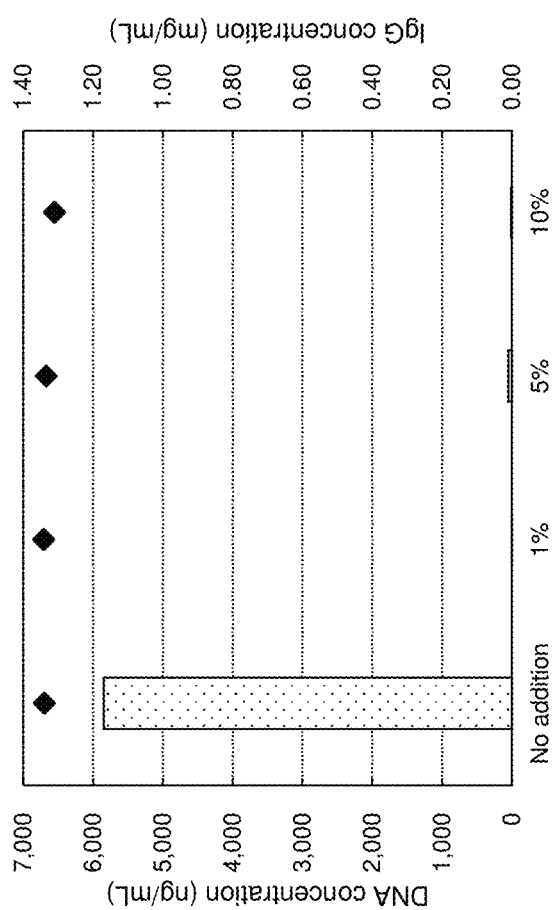

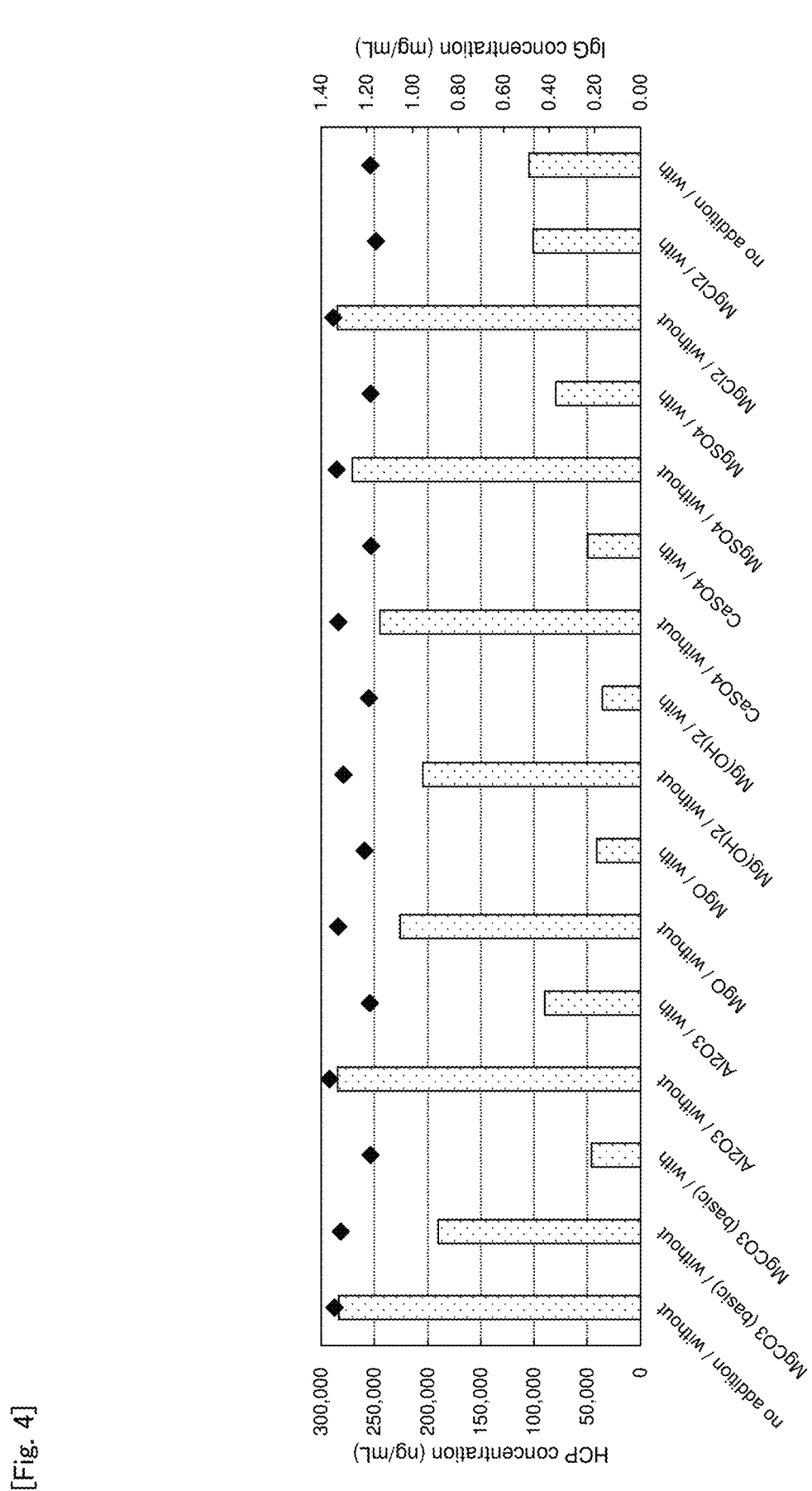
[Fig. 4]

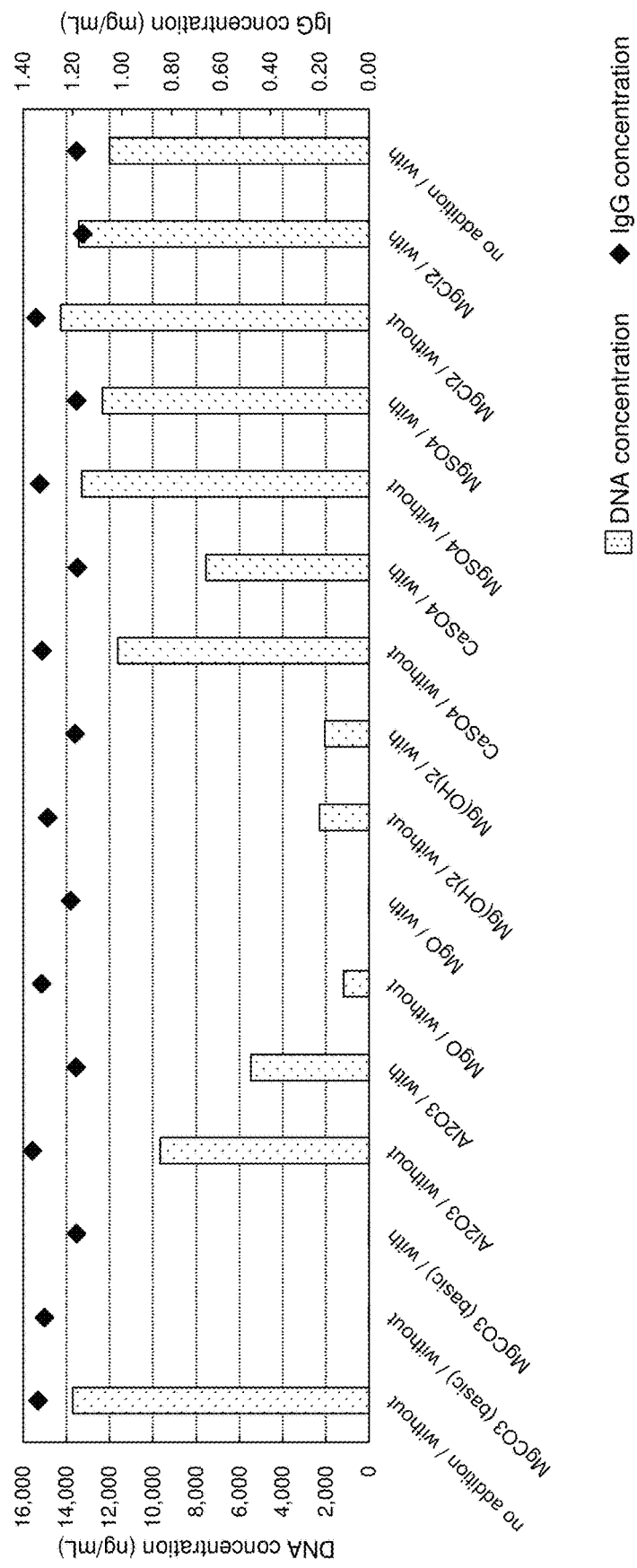
[Fig. 5]

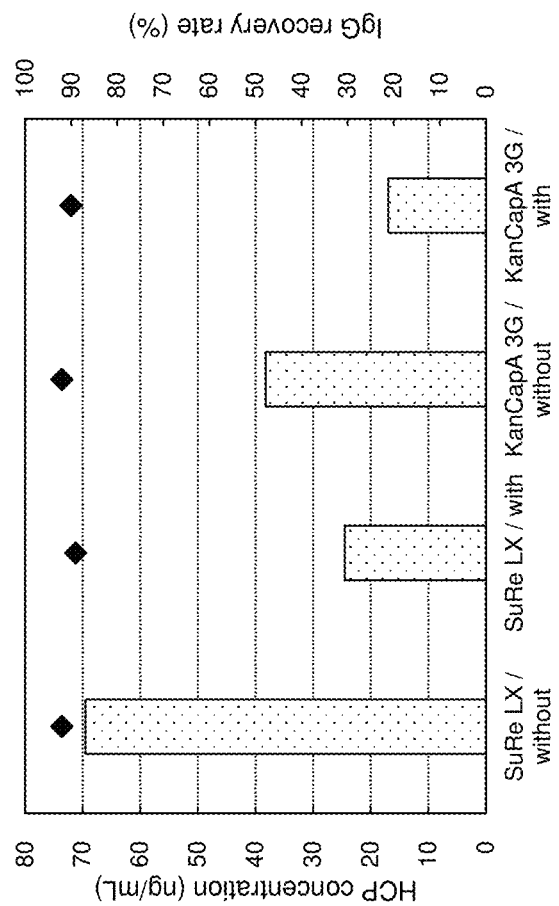
[Fig. 6]

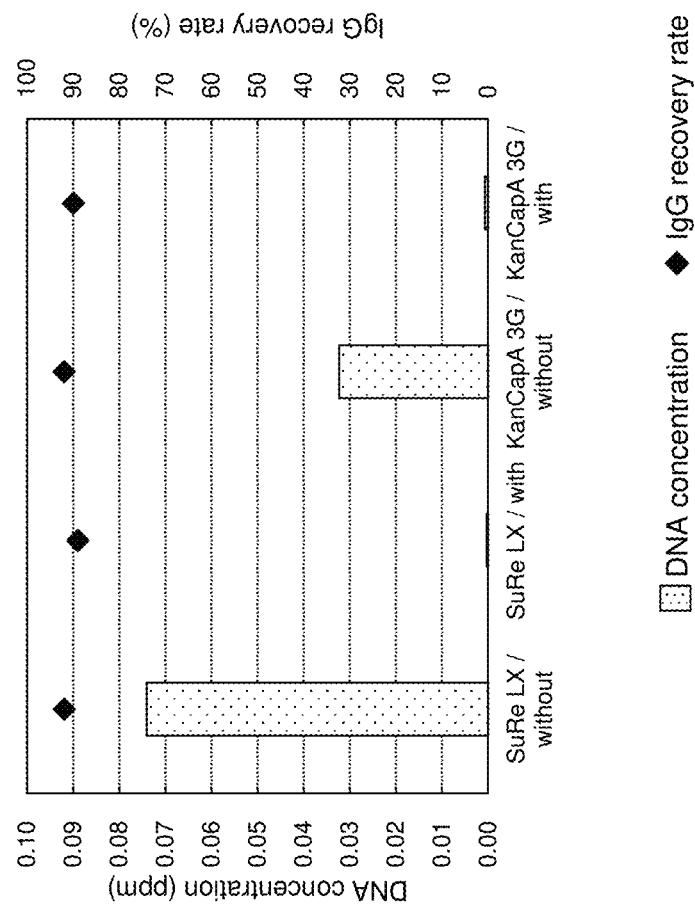
[Fig. 7]

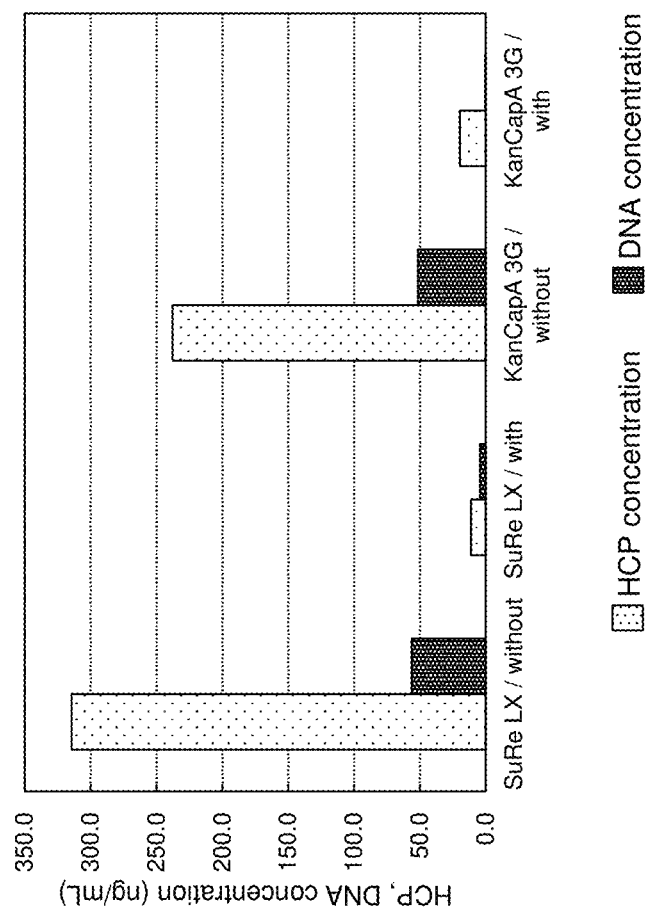
[Fig. 8]

[Fig. 9]
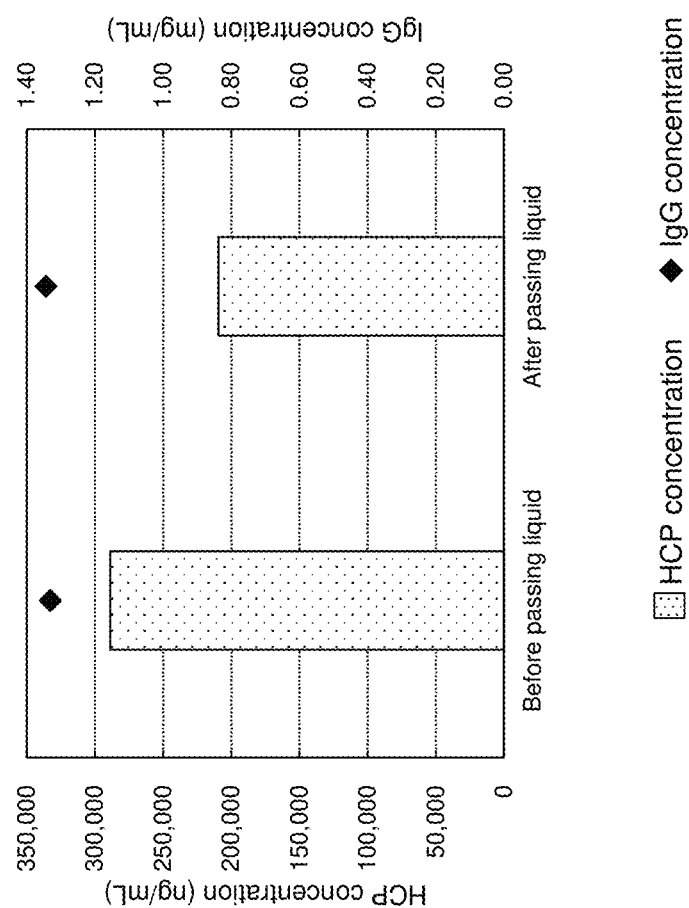

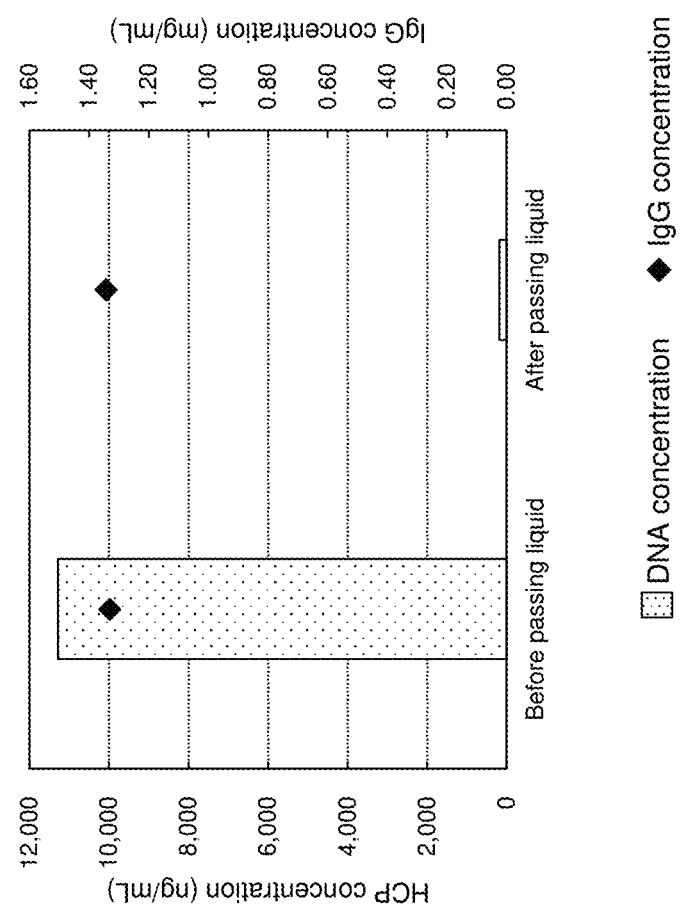
[Fig. 10]

METHOD FOR PURIFYING ANTIBODY OR ANTIBODY-LIKE MOLECULE

TECHNICAL FIELD

The present invention relates to a method for improving a purity of a target antibody or an antibody-like molecule by reducing an impurity from a composition containing the impurity.

BACKGROUND ART

A useful protein such as an antibody produced by an extraction from a living body sample or a gene recombination technology is recently used for many applications such as a pharmaceutical product, a food, an industrial enzyme, an adsorbent and a sensor, and it has become an issue to efficiently purify a useful protein with high purity. Since an impurity often has a harmful effect on a function of a target protein and causes a side effect, an impurity is needed to be removed and a useful protein should be purified with high purity in order to ensure an effectivity and a safety of the useful protein. For example, a gene of a host cell such as an animal cell, a plant cell and a bacterial cell is recombined by gene recombination technology to produce a target useful protein and the useful protein is purified with high purity in a bio-pharmaceutical product field using a useful protein such as a recombinant protein and a peptide as an active component. A useful protein produced by cultivating a recombinant animal cell, plant cell or bacterial cell is secreted in a supernatant of the culture fluid, expressed as a soluble protein in a cell, or expressed as an insoluble protein in an intracellular inclusion. A useful protein expressed in a supernatant of a culture fluid is separated from a host animal cell, plant cell or bacterial cell, a fragment thereof, or other insoluble components by a centrifugation treatment or a membrane treatment, and then purified with high purity by chromatography or a membrane separation process. A useful protein expressed as a soluble protein in a cell is extracted by dissolving or disrupting the cell, separated from an insoluble component by a centrifugation treatment or a membrane treatment, and then purified with high purity by chromatography or a membrane separation process. A useful protein expressed as an insoluble protein in a cell is extracted by dissolving or disrupting the cell, a soluble component is removed by a centrifugation treatment or a membrane treatment, the useful protein is dissolved from the remaining residue to obtain a useful protein solution containing an impurity, and the useful protein is purified with high purity by chromatography or a membrane separation process.

Since a useful protein solution to be subjected to chromatography or a membrane separation process contains a large amount of an impurity such as a contaminating protein derived from a host, nucleic acid, membrane fragment derived from cell and organelle, and culture medium component, a heavy load is applied to chromatography and a membrane separation process. As a result, adsorption capacity of chromatography carrier is decreased, separation capacity is decreased, processing speed is decreased due to an increase of back pressure, and a carrier life is shorten due to a decrease of washing efficiency and regenerating efficiency. Also, in a membrane separation process, a processing capacity per a unit membrane area is decreased, back pressure is increased, processing speed is decreased, and a carrier life is shorten due to a decrease of washing efficiency and regenerating efficiency. Since a large amount of an impurity gives a heavy load to purification with high purity by chromatography and a membrane separation process, a decrease of an impurity before such treatments is important for a load reduction to a latter process.

As a technology to treat a useful protein solution containing an impurity and decrease the impurity, a method to add a water-soluble additive such as polyamine (Non-patent document 1), chitosan (Non-patent document 2), a divalent cation which is liberated under low pH (Patent document 1), poly(diallyldimethylammonium chloride) (PDACMAC, Non-patent document 3) and an endonuclease (Non-patent document 4), and a method to precipitate an impurity to be removed by pH adjustment (Non-patent document 5) or heat treatment (Patent document 2) are known.

A water-soluble additive has a problem of a removal in latter step, since a useful protein such as an antibody is generally purified in an aqueous system. In addition, a construction of a latter process to remove an impurity is difficult and there are problems of a safety and a numerical value control of a residual material, since, for example, an additive and a fragment thereof are adsorbed on a useful protein. For example, a useful protein used for a pharmaceutical product must be highly purified in terms of safety, and Food and Drug Administration requires to observe Q3A guideline to strictly control a residual impurity. An endonuclease is preferred on the point that an endonuclease can be easily removed by adjusting a condition of chromatography to remove an impurity such as other contaminating protein. On the one hand, although an endonuclease fragments DNA to be disabled and such a fragmented DNA can be efficiently removed by chromatography and a membrane separation, an endonuclease is not sufficient as a means to remove an impurity since an endonuclease cannot improve an efficiency to remove a contaminating protein or the like. Adjustment of pH and heat treatment have high risk of function depression, denaturation, aggregation and degradation of a target useful protein, and have problems of a strict control of a step parameter and removal of an impurity such as an aggregate, a fragment and a modified protein which impurity is derived from a target protein and generated by the treatment.

PRIOR ART DOCUMENT

Patent Document

Patent document 1: JP 2010-508352 T
Patent document 2: JP S63-275600 A

Non-Patent Document

Non-patent document 1: Peram T, et al., Biotechnol Prog, 26(5): 1322-1331
Non-patent document 2: Riske F, et al., J. Biotechnol, 128(4): 813-823
Non-patent document 3: McNerney T, et al., $241^{st}$ ACS National Meeting & Exposition, Anaheim, Calif., BIOT-302
Non-patent document 4: D. W. Zabriskie, et al., Biotechnology and Bioengineering, Vol. 32, 100-104
Non-patent document 5: Hjelm, et al., FEBS. LETT., 1972, 28: 73-76

DISCLOSURE OF THE INVENTION

Problems to be Solved by the Invention

A highly water-soluble additive is used for purifying a useful protein such as an antibody in many of the above-described conventional arts, and the conventional arts have problems of difficult removal of the additive and a degradant thereof from a target useful protein in a latter process and control of a residual material. Adjustment of pH and heat treatment have problems as a roughly purifying means before a purification with high purity, since adjustment of pH and heat treatment have a risk of function depression, denaturation, aggregation and degradation of a target useful protein, and a strict control of a step parameter and removal of an impurity such as an aggregate, a fragment and a modified protein which impurity is derived from a target protein and generated by the treatment.

Accordingly the objective of the present invention is to provide an additive which is effective for removing an impurity from a useful protein such as an antibody and which can reduce a load on a latter process, and a utilization method thereof.

Means for Solving the Problems

The inventors of the present invention repeated intensive studies in order to solve the above-described problems. As a result, the inventors completed the present invention by finding that not only an impurity can be effectively reduced with maintaining a target antibody or an antibody-like molecule in an aqueous solution by adding the specific water-insoluble organic compound to an aqueous solution or a suspension containing the antibody or antibody-like molecule and an impurity but also the water-insoluble organic compound can be easily separated from the system by spontaneous precipitation, centrifugation, membrane separation or the like.

The present invention is hereinafter described.

[1] A method for purifying an antibody or an antibody-like molecule,
    the method comprising the step of treating an aqueous solution or a suspension comprising the antibody or the antibody-like molecule and an impurity with a water-insoluble inorganic compound,
    wherein the water-insoluble inorganic compound comprises one or more elements selected from magnesium, calcium and aluminum.
[2] The method according to the above [1], wherein the water-insoluble inorganic compound is one or more selected from magnesium carbonate, magnesium hydroxide, magnesium oxide, magnesium phosphate, calcium sulfate and aluminum oxide.
[3] The method according to the above [1] or [2], further comprising the step of contacting the aqueous solution or the suspension with an activated carbon.
[4] The method according to any one of the above [1] to [3], wherein the aqueous solution or the suspension is a culture fluid comprising the antibody or the antibody-like molecule.
[5] The method according to any one of the above [1] to [3], wherein the aqueous solution or the suspension is a culture supernatant obtained by a centrifugation treatment or a membrane treatment of a culture fluid.
[6] The method according to the above [4] or [5], wherein the culture fluid is a culture fluid for a recombinant host cell to produce the antibody or the antibody-like molecule.
[7] The method according to any one of the above [1] to [3], wherein the aqueous solution or the suspension is a homogenate or an extract of a recombinant host cell.
[8] The method according to any one of the above [1] to [3], wherein the aqueous solution or the suspension is a supernatant obtained by subjecting a homogenate or an extract of a recombinant host cell to a centrifugation treatment or a membrane treatment.
[9] The method according to any one of the above [1] to [3], wherein the aqueous solution or the suspension is an extract derived from a living body.
[10] The method according to any one of the above [1] to [9], wherein the antibody or the antibody-like molecule is an Fc-containing protein.
[11] The method according to any one of the above [1] to [10], wherein the antibody or the antibody-like molecule is a low molecular weight antibody.
[12] The method according to any one of the above [1] to [11], further comprising the step of treating the aqueous solution or the suspension with a flocculant.
[13] The method according to any one of the above [1] to [12], further comprising the step of treating the aqueous solution or the suspension with an endonuclease.
[14] The method according to any one of the above [1] to [13], further comprising the step of subjecting the purified antibody or the purified antibody-like molecule to a column treatment or a membrane filtration treatment.

Effect of the Invention

An impurity can be efficiently removed from an aqueous solution or a suspension which contains the impurity and an antibody or an antibody-like molecule by the present invention using the specific water-insoluble inorganic compound. Not only a roughly purified product can be obtained even by the present invention method only but also when the present invention method is combined with the other high purification process, the load on the latter purification process can be reduced.

BRIEF DESCRIPTION OF THE DRAWINGS

FIG. 1 is a graph to show the effect to reduce an impurity amount by the present invention method and a conventional method.

FIG. 2 is a graph to show the relationship between the amount of basic magnesium carbonate as the water-insoluble inorganic compound, and IgG concentration and a remaining amount of host cell protein (HCP) as an impurity.

FIG. 3 is a graph to show the relationship between the amount of added basic magnesium carbonate as the water-insoluble inorganic compound, and IgG concentration and a remaining amount of DNA as an impurity.

FIG. 4 is a graph to show the relationship between various water-insoluble inorganic compounds only or the combination of the water-insoluble inorganic compound with an activated carbon, and IgG concentration and a remaining amount of HCP as an impurity.

FIG. 5 is a graph to show the relationship between various water-insoluble inorganic compounds only or the combination of the water-insoluble inorganic compound with an activated carbon, and IgG concentration and a remaining amount of DNA as an impurity.

FIG. 6 is a graph to show the relationship between the combination of basic magnesium carbonate as the water-insoluble inorganic compound with a carrier for purifying an antibody, and IgG recovery rate and a remaining amount of HCP as an impurity.

FIG. 7 is a graph to show the relationship between the combination of basic magnesium carbonate as the water-insoluble inorganic compound with a carrier for purifying an antibody, and IgG recovery rate and a remaining amount of DNA as an impurity.

FIG. 8 is a graph to show the relationship between the combination of basic magnesium carbonate as the water-insoluble inorganic compound with a carrier for purifying an antibody, and amounts of HCP and DNA as impurities in a washing liquid for the carrier.

FIG. 9 is a graph to show a HCP concentration and an IgG concentration in the supernatant of a culture fluid before and after the supernatant is passed through the column filled with basic magnesium carbonate.

FIG. 10 is a graph to show a DNA concentration and an IgG concentration in the supernatant of a culture fluid before and after the supernatant is passed through the column filled with basic magnesium carbonate.

MODE FOR CARRYING OUT THE INVENTION

An impurity is removed by treating an aqueous solution or a suspension which comprises the impurity and an antibody or an antibody-like molecule with the specific water-insoluble inorganic compound in the present invention. Each step of the present invention method is hereinafter described, but the present invention is not restricted to the following specific examples.

1. Step to Prepare Antibody/Antibody-Like Molecule-Containing Liquid

An aqueous solution or a suspension comprising an antibody or an antibody-like molecule as a target to be purified is prepared in this step. This step may be arbitrarily implemented, and when the aqueous solution or suspension is already obtained, this step is not needed to be implemented. The aqueous solution means a solution in which the antibody or antibody-like molecule is dissolved in water as a solvent and which does not contain an insoluble component. The suspension means a solution in which the antibody or antibody-like molecule is dissolved in water as a solvent but which contains an insoluble component such as a cell, a disrupted cell, an aggregated component derived from a cell and an aggregate protein. Such an insoluble component may be dispersed or precipitated in the solution.

The "antibody or antibody-like molecule" to be purified in the present invention may be an antibody or an antibody-like molecule which is industrially useful, and may be a functional protein having a polypeptide structure. The protein may have a secondary structure such as alpha helix and beta sheet structure in the molecule, may have a sugar chain, may be modified by a sugar, may be modified by phosphate or tyrosine, or may be coordinated with a metal. In addition, the "antibody or antibody-like molecule" may be a naturally occurring protein and peptide, or produced by genetic engineering technology. The function of a naturally occurring protein and peptide may be improved to be the antibody or antibody-like molecule. The antibody or antibody-like molecule may have a structure of a functional part only, and may be a combination of various functional parts or a combination of the same functional parts. Furthermore, the "antibody or antibody-like molecule" may be crosslinked in the molecule or between the molecules by a disulfide bond between cysteine residues. The "antibody or antibody-like molecule" may contain a subunit structure through a non-covalent bond or may be a connected protein with a chemical modification, and a function may be added to the "antibody or antibody-like molecule" by a chemical modification or an addition of a functional molecule.

The antibody or antibody-like molecule in the present invention is not particularly restricted, and is exemplified by polyclonal antibody, monoclonal antibody, human antibody, humanized antibody, chimeric antibody, single-chain antibody, heavy chain antibody, multivalent antibody, Fab, F(ab'), F(ab')$_2$, Fc, Fc fusion protein, bispecific antibody, heavy chain (H chain), light chain (L chain), single-chain Fv (scFv), sc(Fv)$_2$, disulfide bonded Fv(sdFv), Diabody and antibody-like molecular target peptide (micro antibody). The antibody or antibody-like molecule in the present invention may be preferably any one of an Fc-containing protein such as immunoglobulin and Fc fusion protein containing Fc part, and a low molecular weight antibody such as the above-described Fab, F(ab'), F(ab')$_2$, Fc, heavy chain (H chain), light chain (L chain), single-chain Fv (scFv), sc(Fv)$_2$, disulfide bonded Fv (sdFv), single-chain antibody, heavy chain antibody, multivalent antibody, bispecific antibody, Diabody and antibody-like molecular target peptide (micro antibody).

The "aqueous solution or suspension comprising the antibody or antibody-like molecule and an impurity" to be treated with the specific water-insoluble inorganic compound in the present invention is not particularly restricted as long as the aqueous solution or suspension comprises the antibody or antibody-like molecule and further unwanted component as an impurity. An example of the solution or suspension includes culture fluid, culture supernatant, a suspension obtained by dispersing a cultivated cell or a disrupted cultivated cell, an extract from a cultivated cell or a disrupted cultivated cell in water, and an extract from a living body. The aqueous solution and suspension may also contain an organic solvent. The unwanted component is not particularly restricted as long as the unwanted component is a compound other than the antibody or antibody-like molecule to be purified, and is exemplified by a protein and a nucleic acid derived from a host cell.

The above-described cell to be cultivated may be a naturally occurring cell but is preferably a recombinant host cell. The term "host" is not particularly restricted as long as the host is a cell of an animal, a plant or a bacterium which is used for producing the antibody or antibody-like molecule by recombination, which is transformed using an expression vector or a gene fragment containing DNA encoding the antibody or antibody-like molecule and which can produce the useful protein by expressing the introduced DNA. A gene recombinant cell in the present invention means a host cell transformed by introducing an expression vector or a gene fragment containing a base sequence encoding an amino acid sequence of the target antibody or antibody-like molecule and a promotor which is linked to the base sequence and which is workable in the host cell. The antibody or antibody-like molecule is not particularly restricted as long as the useful protein is expressed by recombination in both of a transient manner and a stationary manner.

An example of a utilizable cell derived from an animal, i.e. animal cell, includes an adhesive cell such as HEK and HeLa; a suspended cell such as 293-F, 293-FT and Jurkat; a cell derived from a mouse, such as CHO and MC; Sf strain derived from *Spodoptera frugiperda*, such as Sf-9 and Sf-21; and an insect cell such as a silkworm cell (Nature, 315, 592-594 (1985)). Among the above examples, CHO cell and HEK cell are preferred.

With respect to a utilizable plant, a system to express a large amount of a heterologous protein in a plant such as rapeseed, corn, potato and banana has been developed, and a cell of such a plant can be preferably utilized.

An example of a utilizable microorganism includes bacteria of which host vector system has been developed, such as Genus *Escherichia*, Genus *Bacillus*, Genus *Pseudomonas*, Genus *Serratia*, Genus *Brevibacterium*, Genus *Corynebacterium*, Genus *Brevibacillus*, Genus *Streptococcus* and Genus *Lactobacillus*; an actinomycete of which host vector system has been developed, such as Genus *Rhodococcus* and Genus *Streptomyces*; a yeast of which host vector system has been developed, such as Genus *Saccharomyces*, Genus *Kluyveromyces*, Genus *Schizosaccharomyces*, Genus *Zygosaccharomyces*, Genus *Yarrowia*, Genus *Trichosporon*, Genus *Rhodosporidium*, Genus *Pichia* and Genus *Candida*; and a fungus of which host vector system has been developed, such as Genus *Neurospora*, Genus *Aspergillus*, Genus *Cephalosporium* and Genus *Trichoderma*. The above microorganism is not particularly restricted and may be both of a gram-negative microorganism and a gram-positive microorganism. A gram-negative microorganism is preferably exemplified by *Escherichia coli*, and a gram-positive microorganism is preferably exemplified by a yeast and a *Brevibacillus* bacterium.

A culture fluid of a recombinant host cell as described above, a homogenate or an extract of a recombinant host cell, and a culture fluid supernatant obtained therefrom by a centrifugation treatment or a membrane treatment can be preferably used as the "aqueous solution or suspension comprising the antibody or the antibody-like molecule and an impurity" in the present invention. The culture fluid of a recombinant host cell, homogenate or extract of a recombinant host cell, culture fluid supernatant obtained therefrom by a centrifugation treatment or a membrane treatment, and other extract derived from a living body sample contain a large amount of an unwanted impurity in addition to the target antibody or antibody-like molecule. An example of such an impurity includes a cell, a cell fragment, a membrane fragment of an organelle, a contaminating protein, a fragment thereof and an aggregate thereof, an aggregate of a protein, a lipid such as a cell wall substance, a nucleic acid such as a chromosomal DNA and an extrachromosomal DNA, a ribonucleic acid such as t-RNA and mRNA, a culture medium component, and a combination thereof. For example, when the antibody or antibody-like molecule is a recombinant protein, the recombinant protein is expressed at a different site depending on the kind of a host. For example, a certain host secretes an expressed protein outside the cell, and other certain host expresses and accumulates a protein in the cell. Many gram-negative bacteria can accumulate the target antibody or antibody-like molecule in periplasmic space between an inner cell membrane and an outer membrane. When the antibody or antibody-like molecule is expressed in a periplasmic space or in a cell of a host, it is needed to extract the target antibody or antibody-like molecule by dissolving a membrane component of a host cell or disrupting a host cell. When the antibody or antibody-like molecule is expressed in a host as an insoluble fraction such as an inclusion body, the antibody or antibody-like molecule is needed to be extracted from a residue obtained by recovering a host cell with a centrifugation treatment or a membrane treatment and then dissolving or disrupting the host cell to remove an insoluble fraction with a centrifugation treatment or a membrane treatment.

As a solvent of the above-described aqueous solution and suspension, an aqueous solution such as a buffer solution in addition to water may be used. An example of such a buffer solution includes a buffer solution containing phosphate, citrate, 2-(N-morpholino)ethanesulfonic acid (MES), Bis-Tris, N-(2-Acetamido)iminodiacetic acid (ADA), Piperazine-1,4-bis(2-ethanesulfonic acid) (PIPES), N-(2-Acetamido)-2-aminoethanesulfonic acid (ACES), 3-(N-Morpholino)-2-hydroxypropanesulfonic acid (MOPSO), N,N-Bis(2-hydroxyethyl)-2-aminoethanesulfonic acid (BES), 3-(N-morpholino)propanesulfonic acid (MOPS), N-Tris(hydroxymethyl)methyl-2-aminoethanesulfonic acid (TES), 4-(2-hydroxyethyl)-1-piperazineethanesulfonic acid (HEPES), Triethanolamine, 3-[4-(2-hydroxyethyl)-1-piperazinyl]propanesulfonic acid (EPPS), Tricine, Tris, Glycylglycine, Bicine, N-Tris(hydroxymethyl)methyl-3-aminopropanesulfonic acid (TAPS), and Dulbecco's phosphate buffered saline. A pH value during the treatment of the aqueous solution or dispersion comprising the antibody or antibody-like molecule and an impurity with the water-insoluble inorganic compound is preferably 4 or more and 12 or less, and more preferably 5 or more and 10 or less.

2. Water-Insoluble Inorganic Compound Treatment Step

In this step, the antibody or antibody-like molecule is purified by treating the aqueous solution or suspension comprising the antibody or antibody-like molecule and an impurity with the water-insoluble inorganic compound comprising 1 or more elements selected from magnesium, calcium and aluminum to selectively adsorb the impurity other than the antibody or antibody-like molecule to be purified. The term "purify" means that a ratio of an impurity to the antibody or antibody-like molecule in the aqueous solution or suspension before being contacted with the water-insoluble inorganic compound is reduced. The term "treatment" means that the aqueous solution or suspension comprising the antibody or antibody-like molecule and an impurity is contacted with the water-insoluble inorganic compound. The aqueous solution or suspension comprising the antibody or antibody-like molecule and an impurity is hereinafter abbreviated as "the antibody-containing liquid" in some cases.

The term "water-insoluble" in this disclosure means a degree to which an inorganic compound powder is dissolved within 30 minutes under a condition where the powder is added in purified water and the mixture is strongly shaken up at 20±5° C. for 30 seconds every 5 minutes, and specifically means an amount of purified water required to dissolve 1 g of the organic compound is 100 mL or more.

The water-insoluble inorganic compound comprises 1 or more elements selected from magnesium, calcium and aluminum, is exemplified by an insoluble carbonate, an insoluble sulfate, an insoluble phosphate and an oxide of the above metal, and is preferably 1 or more selected from magnesium carbonate, magnesium hydroxide, magnesium oxide, calcium sulfate, magnesium phosphate and aluminum oxide, and more preferably a water-insoluble magnesium salt. For example, basic magnesium carbonate, which is a mixture of magnesium hydroxide and magnesium carbonate, is also preferably used. On the one hand, a phosphate salt, such as calcium phosphate, other than magnesium phosphate is not preferred, since a water solubility thereof is relatively high and such a phosphate salt may possibly adsorb the target antibody or antibody-like molecule.

In particular, several gram of magnesium carbonate is administered per 1 day as an ethical pharmaceutical to treat gastric ulcer and duodenal ulcer, gastritis such as acute gastritis, chronic gastritis and drug-induced gastritis, abnormal upper gastrointestinal function such as neurogenic anorexia, gastroptosis and gastric hyperacidity, and costiveness, and a safety of magnesium carbonate is confirmed. In addition, magnesium carbonate is excellent, since magnesium carbonate can be readily removed by a stationary precipitation, centrifugation or a membrane separation, and a small amount of a leakage thereof can be separated from the antibody or antibody-like molecule by a membrane separation or chromatography.

A size of the water-insoluble inorganic compound may be appropriately adjusted, and for example, an average particle diameter thereof may be adjusted to 0.1 μm or more and 1000 μm or less. When the average particle diameter is 1000 μm or less, an impurity can be adsorbed more efficiently due to a sufficiently large specific surface area of the water-insoluble inorganic compound. When the average particle diameter is 0.1 μm or more, an excessive energy for pulverization is not needed. In addition, the average particle diameter is preferably 1 μm or more in terms of handleability during filling into a column. The average particle diameter is measured using a laser diffraction particle size distribution analyzer in this disclosure. Such an average particle diameter is based on volume, weight, number or the like, and is preferably based on volume.

A usage amount of the water-insoluble inorganic compound may be adjusted depending on a concentration of the antibody-containing liquid or the like, and for example, 0.1 g or more and 20 g or less of the water-insoluble inorganic compound to 100 mL of the antibody-containing liquid may be used. The ratio is preferably 15 g/100 mL or less. In addition, 0.1 mass % or more and 20 mass % or less of the water-insoluble inorganic compound to the antibody-containing liquid may be used, and the ratio is preferably 1 mass % or more and 15 mass % or less.

In general, as a method for separating a culture fluid or the like containing the antibody or antibody-like molecule from a cultivated host cell or a cultivated host cell fragment, a living body sample, a culture fluid or an extract is left to stand or subjected to centrifugation, dead-end filtration, cross-flow filtration or acoustic wave separation, and then a clarified liquid is recovered to be separated from a host cell or a host cell fragment as a clarification step. The purification method of the present invention can be preferably used independently or in combination with the above-described clarification step. The above-described treatment by dead-end filtration, cross-flow filtration or acoustic wave separation and the purification by the present invention may be carried out after the culture fluid or extract is centrifuged, or the culture fluid or extract may be directly subjected to the treatment or the purification.

During the above-described dead-end filtration, a feed solution flows in a direction perpendicular to a membrane, and a filtrate passes through the membrane. A method for recovering a solution containing the antibody or antibody-like molecule by dead-end filtration is exemplified by microfiltration and ultrafiltration using a bottle top filter and a centrifugal filter unit, and is not restricted thereto.

During the above-described cross-flow filtration, a feed solution flows in a direction parallel to a membrane, and a filtrate passes through the membrane. A method for recovering a solution containing the antibody or antibody-like molecule by cross-flow filtration is exemplified by microfiltration and ultrafiltration using a cassette membrane and a hollow fiber, and is not restricted thereto.

The above-described treatment by acoustic wave separation means a method for separating an insoluble substance and a supernatant in a feed solution by applying standing wave to the feed solution so that the insoluble substance is assembled at the node of the standing wave to be precipitated. A method for recovering a solution containing the antibody or antibody-like molecule by acoustic wave separation is exemplified by a method for treating the solution containing the antibody or antibody-like molecule using an acoustic wave separator, and is not restricted thereto.

A bottle top filter to carry out the dead-end filtration is exemplified by Nalgene Rapid-Flow PES coated sterile disposable bottle top filter 0.45 μm (manufactured by Thermo Scientific), Nalgene Rapid-Flow PES coated sterile disposable bottle top filter 0.2 μm (manufactured by Thermo Scientific), IWAKI bottle top filter 500 mL PES 0.22 μm 33 bore (manufactured by AGC TECHNO GLASS•IWAKI), Bottle top vacuum filter 0.22 μm (manufactured by Corning) and Bottle top vacuum filter 0.45 μm (manufactured by Corning), and is not restricted thereto.

A centrifugal filter unit to carry out the dead-end filtration is exemplified by Vivaspin 20-3K (manufactured by GE Healthcare Life Sciences), Vivaspin 20-5K (manufactured by GE Healthcare Life Sciences), Vivaspin 20-10K (manufactured by GE Healthcare Life Sciences), Vivaspin 20-30K (manufactured by GE Healthcare Life Sciences), Vivaspin 20-50K (manufactured by GE Healthcare Life Sciences), Vivaspin 20-100K (manufactured by GE Healthcare Life Sciences), Amicon Ultra-15 3 kDa (manufactured by MERCK MILLIPORE), Amicon Ultra-15 10 kDa (manufactured by MERCK MILLIPORE), Amicon Ultra-15 30 kDa (manufactured by MERCK MILLIPORE), Amicon Ultra-15 50 kDa (manufactured by MERCK MILLIPORE) and Amicon Ultra-15 100 kDa (manufactured by MERCK MILLIPORE), and is not restricted thereto.

A cassette membrane to carry out the cross-flow filtration is exemplified by PelliconXL 50 microfiltration module 0.65 μm (manufactured by MERCK MILLIPORE), PelliconXL 50 microfiltration module 0.22 μm (manufactured by MERCK MILLIPORE), PelliconXL 50 microfiltration module 0.45 μm (manufactured by MERCK MILLIPORE), PelliconXL 50 microfiltration module 0.10 μm (manufactured by MERCK MILLIPORE), Kvick Start 50 cm$^2$, 5 KD, PES (manufactured by GE Healthcare Life Sciences), Kvick Start 50 cm$^2$, 10 KD, PES (manufactured by GE Healthcare Life Sciences), Kvick Start 50 cm$^2$, 30 KD, PES (manufactured by GE Healthcare Life Sciences), Kvick Start 50 cm$^2$, 50 KD, PES (manufactured by GE Healthcare Life Sciences), Kvick Start 50 cm$^2$, 100 KD, PES (manufactured by GE Healthcare Life Sciences), Pellicon2 Cassette-Biomax® Hydrophilic Polyethersulfone Membrane•A Screen 5 kDa (manufactured by MERCK MILLIPORE), Pellicon2 Cassette-Biomax® Hydrophilic Polyethersulfone Membrane•A Screen 8 kDa (manufactured by MERCK MILLIPORE), Pellicon2 Cassette-Biomax® Hydrophilic Polyethersulfone Membrane•A Screen 10 kDa (manufactured by MERCK MILLIPORE), Pellicon2 Cassette-Biomax® Hydrophilic Polyethersulfone Membrane•A Screen 30 kDa (manufactured by MERCK MILLIPORE), Pellicon2 Cassette-Biomax® Hydrophilic Polyethersulfone Membrane•A Screen 50 kDa (manufactured by MERCK MILLIPORE) and Pellicon2 Cassette-Biomax® Hydrophilic Polyethersulfone Membrane•A Screen 100 kDa (manufactured by MERCK MILLIPORE), and is not restricted thereto.

A hollow fiber to carry out the cross-flow filtration is exemplified by MidGee Cartridge, 0.1 micron (manufactured by GE Healthcare Life Sciences), MidGee Cartridge, 0.2 micron (manufactured by GE Healthcare Life Sciences), MidGee Cartridge, 0.45 micron (manufactured by GE Healthcare Life Sciences), MidGee Cartridge, 0.65 micron (manufactured by GE Healthcare Life Sciences), MidGee Cartridge, 1 kD (manufactured by GE Healthcare Life Sciences), MidGee Cartridge, 3 kD (manufactured by GE Healthcare Life Sciences), MidGee Cartridge, 10 kD (manufactured by GE Healthcare Life Sciences), MidGee Cartridge, 30 kD (manufactured by GE Healthcare Life Sciences), MidGee Cartridge, 50 kD (manufactured by GE Healthcare Life Sciences) and MidGee Cartridge, 100 kD (manufactured by GE Healthcare Life Sciences), and is not restricted thereto.

The acoustic wave separation is exemplified by Cadence Acoustic Separator (manufactured by PALL), and is not restricted thereto.

A method for contacting the antibody-containing liquid with the water-insoluble inorganic compound may be appropriately selected. For example, the water-insoluble inorganic compound is added to the antibody-containing liquid, and the mixture may be shaken or stirred. A temperature at the time may be an ordinary temperature, and can be specifically adjusted to 0° C. or higher and 40° C. or lower. The temperature is preferably 1° C. or higher, more preferably 10° C. or higher or 15° C. or higher, and preferably 30° C. or lower, more preferably 25° C. or lower. A time for the contact can be adjusted to 1 second or more and 10 hours or less.

After the contact, the water-insoluble inorganic compound may be separated from the antibody-containing liquid by centrifugation, filtration or the like. At the time, the antibody or antibody-like molecule is mainly dispersed in a liquid part, and all or a part of the impurity other than the antibody or antibody-like molecule is adsorbed on the water-insoluble inorganic compound. A part of the antibody or antibody-like molecule may be adsorbed on the water-insoluble inorganic compound and a part of the impurity other than the antibody or antibody-like molecule may be dissolved in a liquid part in some cases, but at least a total amount of the impurity in the liquid part can be reduced and the antibody or antibody-like molecule in the liquid part is concentrated.

The impurity adsorbed on the water-insoluble inorganic compound in this step is not particularly restricted as long as the impurity is a compound other than the antibody or antibody-like molecule, and is exemplified by an aggregated antibody or an aggregated antibody-like molecule, a contaminant from a host cell, and a contaminant derived from cell cultivation. An example of such a contaminant from a host cell includes a nucleic acid derived from a host cell, a plasmid, and a protein derived from a host cell. An example of such a contaminant derived from cell cultivation includes a culture medium component, serum albumin and other serum protein, and a plasmid DNA for transfection.

In addition, the impurity other than the antibody or antibody-like molecule may be adsorbed on the water-insoluble inorganic compound by filling a column with the water-insoluble inorganic compound and passing the antibody-containing liquid through the column. The adsorption of an impurity and the separation of a liquid part from the water-insoluble inorganic compound can be concurrently carried out in such a case. An amount of the water-insoluble inorganic compound to fill a column and a flow rate of the antibody-containing liquid are preferably adjusted so that an impurity is sufficiently adsorbed on the water-insoluble inorganic compound.

3. Step to Contact with Activated Carbon

In this step, the aqueous solution or suspension comprising the antibody or antibody-like molecule and an impurity is contacted with an activated carbon. This step may be carried out before or after the above-described treatment step, or the steps may concurrently be carried out by using the water-insoluble inorganic compound and an activated carbon in combination. This step may be optionally carried out.

An activated carbon is obtained by burning a charcoal, a palm shell or the like to develop a pore to be porous, and is excellent in adsorption performance. A general specific surface area of an activated carbon is about 800 $m^2/g$ or more and about 2500 $m^2/g$ or less.

An example of an activated carbon includes a mineral activated carbon and a plant activated carbon. An example of such a mineral activated carbon includes a coal activated carbon and a petroleum activated carbon. An example of such a plant activated carbon includes a wood activated carbon and a palm shell activated carbon, and a wood activated carbon is preferred.

A raw material of an activated carbon is not particularly restricted as long as the raw material is a carbonaceous substance, and is exemplified by a woodiness such as sawdust, charcoal, ash, herbaceous peat, peat and wood chip; palm shell; a coal such as lignite, brown coal and anthracite; petroleum pitch; and an organic compound such as rayon, acrylonitrile and a phenolic resin.

A method for producing an activated carbon is not particularly restricted and is exemplified by a chemical liquid activation method and a gas activation method. In a chemical liquid activation method, zinc chloride, phosphoric acid or the like is added to a raw material at high temperature and a mixture is subjected to carbonization reaction at high temperature. In a gas activation method, a mixture of a carbonized raw material and a gas such as water vapor, carbon dioxide, air and combustion gas is reacted at high temperature. An example of the method preferably includes a zinc chloride activation method, an acid activation method using phosphoric acid, and a water vapor activation method.

A figure of an activated carbon is not particularly restricted, and an example of an activated carbon includes a granular activated carbon such as pulverized charcoal, granular charcoal, spherical charcoal and pellet charcoal; a fibrous activated carbon such as fiber and cloth; a specially formed activated carbon such as sheet, formed body and honeycomb; and a powder activated carbon.

Also, an activated carbon to which a charge of plus or minus is added and an activated carbon which is modified with a surface-modifying agent such as poly(hydroxyethyl methacrylate) (PHEMA), heparin, cellulose and polyurethane can be used in the purification method of the present invention. In addition, a carbon gel prepared by sol-gel method is included in the activated carbon usable in the purification method of the present invention. An example of a raw material used in the sol-gel method includes phenol, melamine, resorcinol and formaldehyde.

An average pore diameter of an activated carbon is not particularly restricted, and is generally 0.1 nm or more and 20 nm or less, preferably 0.5 nm or more and 5.0 nm or less, more preferably 2.0 nm or more and 5.0 nm or less, and even more preferably 3.0 nm or more and 5.0 nm or less. An average pore diameter of an activated carbon can be calculated from an adsorption isothermal curve of nitrogen gas using BJH method.

A means of a purification method using an activated carbon according to the present invention is not particularly restricted, and is exemplified by a batch method, a membrane treatment method and a column chromatography method. An appropriate figure of an activated carbon is selected depending on each of means. An activated carbon may be used in the forms of a particle prepared by enclosing an activated carbon in porous polymer or gel, a membrane prepared by adsorbing, immobilizing or forming an activated carbon using a fiber or a supporting agent such as polypropylene and cellulose, and a cartridge, as needed.

A membrane or a cartridge containing an activated carbon is specifically exemplified by CUNO activated carbon filter cartridge and Zeta Plus activated carbon filter cartridge (manufactured by Sumitomo 3M, CUNO and Zeta Plus are registered trademarks); Millistak+ activated carbon filter (manufactured by Merck Millipore, Millistak is a registered trademark); Supra AKS1 filter, AKS1 filter, Stax™, AKS1 (manufactured by Pall); Ad'All (manufactured by UNITIKA); K Filter®, activated carbon sheet (manufactured by TOYOBO); Hemax (manufactured by Kuraray); Hemosorba® (manufactured by Asahi Kasei Medical); Hemocolumn (manufactured by TERUMO); and Hemocells (manufactured by TEIJIN), and is not restricted thereto. An example of a membrane or a cartridge containing a wood-based activated carbon among the above examples includes Zeta Plus activated carbon filter cartridge (manufactured by Sumitomo 3M, Zeta Plus is a registered trademark); Supra AKS1 filter, AKS1 filter, Stax™, AKS1 (manufactured by Pall).

A packing density, a particle size, a hardness, a weight loss on drying, an ignition residue, a specific surface area, a pore volume or the like of an activated carbon to be used can be appropriately selected.

A usage amount of an activated carbon may be adjusted depending on a concentration of the antibody-containing liquid or the like, and for example, 0.5 g or more and 5 g or less of an activated carbon to 100 mL of the antibody-containing liquid may be used.

As a method for contacting the antibody-containing liquid with an activated carbon, similarly to the case of the water-insoluble inorganic compound, an activated carbon is added to the antibody-containing liquid and the mixture may be shaken or stirred, or a column is filled with an activated carbon. When this step and the above-described treatment step are concurrently carried out, the water-insoluble inorganic compound and an activated carbon may be mixed to be used.

4. Flocculant Treatment Step

In this step, the aqueous solution or suspension comprising the antibody or antibody-like molecule and an impurity is treated with a flocculant. This step may be carried out before or after the water-insoluble inorganic compound treatment step and/or the step to contact with activated carbon, or may be concurrently carried out by using the water-insoluble inorganic compound and/or an activated carbon and a flocculant in combination. This step may be optionally carried out.

An example of the flocculant includes caprylic acid, polyamine, a divalent cation, polyetherimine, chitosan, polyethyleneglycol, polyvinyl alcohol, polyvinylpyrrolidone and pDACMAC. An example of the divalent cation includes $Ca^{2+}$, $Mg^{2+}$, $Cu^{2+}$, $Co^{2+}$, $Mn^{2+}$, $Ni^{2+}$, $Be^{2+}$, $Sr^{2+}$, $Ba^{2+}$, $Ra^{2+}$, $Zn^{2+}$, $Cd^{2+}$, $Ag^{2+}$, $Pd^{2+}$ and $Rh^{2+}$, and the divalent cation can be used in the free state or as a hydrochloride salt, a sulfate salt, a citrate salt or the like.

A usage amount of a flocculant may be adjusted depending on a concentration of the antibody-containing liquid or the like, and when the flocculant is polyamine or polyetherimine, 0.01 w/v % or more and 10 w/v % or less of the flocculant may be used, and 0.1 w/v % or more and 1 w/v % or less of the flocculant may be preferably used. When the flocculant is caprylic acid, chitosan, polyethyleneglycol, polyvinyl alcohol or polyvinylpyrrolidone, 0.01 w/v % or more and 10 w/v % or less of the flocculant may be used, and 1 w/v % or more and 5 w/v % or less of the flocculant may be preferably used. When the flocculant is pDACMAC, 0.01 w/v % or more and 0.1 w/v % or less of the flocculant may be used, and 0.1 w/v % or more and 0.5 w/v % or less of the flocculant may be preferably used. When the flocculant is a divalent cation, a divalent cation may be added in a concentration of 1 mM or more and 100 mM or less, and more preferably 2 mM or more and 50 mM or less.

As a method for contacting the antibody-containing liquid with a flocculant, similarly to the case of the water-insoluble inorganic compound, a flocculant is added to the antibody-containing liquid and the mixture may be shaken or stirred, or a column is filled with a flocculant. When this step and the water-insoluble inorganic compound treatment step and/or the step to contact with activated carbon are concurrently carried out, a flocculant and the water-insoluble inorganic compound and/or an activated carbon may be mixed to be used.

5. Endonuclease Treatment Step

In this step, the aqueous solution or suspension comprising the antibody or antibody-like molecule and an impurity is treated with an endonuclease. This step may be carried out before or after each of the above-described step, or may be concurrently carried out by using an endonuclease and 1 or more selected from the water-insoluble inorganic compound, an activated carbon and a flocculant in combination. This step may be optionally carried out.

An endonuclease is one of DNA-degrading enzymes and has a function to degrade DNA even in the middle part of the base sequence. An example of a commercially available endonuclease includes Benzonase (manufactured by Millipore) and KANEKA endonuclease (manufactured by KANEKA).

A usage amount of an endonuclease may be adjusted depending on a concentration of the antibody-containing liquid or the like and for example, is preferably 10 U/mL or more and more preferably 100 U/mL or more to the antibody-containing liquid. The upper limit thereof is not particularly restricted, and the usage amount is preferably 10,000 U/mL or less.

6. Other Purification Step

The above-described steps can be preferably carried out before or after a general step, such as a membrane treatment and a column treatment described later, to purify the antibody or antibody-like molecule. When the above-described steps are carried out before a membrane treatment and a column treatment, it can be expected to suppress a decrease of an adsorption capacity of a chromatography carrier, a decrease of a separation capacity, a decrease of a processing speed due to an increase of a back pressure, and a decrease of a carrier life due to a decrease in efficiency of washing and regeneration. In addition, also in a membrane filtration process, it can be expected to suppress a decrease of a processing capacity per a unit membrane area, an increase of a back pressure, a decrease of a processing speed, and a decrease of a carrier life due to a decrease in efficiency of washing and regeneration. That is to say, the antibody or antibody-like molecule purified by the above steps may be further treated using a column or a membrane as a preferred embodiment of the present invention. In other words, the purification method of the present invention can be used as a pretreatment of a column treatment and a membrane treatment.

The above-described steps, particularly the above-described treatment step, are excellent as a pretreatment method of a column treatment and a column treatment, since a decrease of an adsorption capacity of a chromatography carrier, a decrease of a separation capacity, a decrease of a processing speed due to an increase of a back pressure, and a decrease of a carrier life due to a decrease in efficiency of washing and regeneration can be expected to be suppressed, and a decrease of a processing capacity per a unit membrane area, an increase of a back pressure, a decrease of a processing speed, and a decrease of a carrier life due to a decrease in efficiency of washing and regeneration can be expected to be also suppressed in a membrane filtration process. In addition, the water-insoluble inorganic compound used in the present invention is industrially very excellent, since the compound is a water-insoluble additive and can be readily removed by spontaneous precipitation, centrifugation or a membrane separation. Furthermore, if a small amount of the compound is leaked, the leakage can be also readily removed ay a membrane separation process or a chromatography process and does not produce a side effect.

The antibody-containing liquid can be subjected to purification by a column treatment such as chromatography. A usable chromatography is not particularly restricted as long as the target antibody or antibody-like molecule can be recovered and purified, and is exemplified by anion exchange chromatography, cation exchange chromatography, hydrophobic chromatography, hydroxyapatite chromatography, mix mode chromatography and affinity chromatography. One of such chromatographies may be used by itself or the chromatographies may be used in combination. The above steps, particularly the above-described treatment step, can be also preferably used before or after the chromatography step.

An anion exchange resin usable in an anion exchange chromatography is not restricted as long as the anion exchange resin exhibits an anion exchanging action. An anion exchange resin is exemplified by Capto Q (manufactured by GE Healthcare Life Sciences), Capto DEAE (manufactured by GE Healthcare Life Sciences), Capto Q ImpRes (manufactured by GE Healthcare Life Sciences), Capto Q Sepharose High Performance (manufactured by GE Healthcare Life Sciences), RESOURCE Q (manufactured by GE Healthcare Life Sciences), SOURCE 30Q (manufactured by GE Healthcare Life Sciences), YMC BioPro Q (manufactured by YMC), YMC BioPro DA (manufactured by YMC), TOYOPEARL SuperQ-650 (manufactured by TOSOH), TOYOPEARL GigaCapQ-650 (manufactured by TOSOH), TOYOPEARL DEAE-650 (manufactured by TOSOH), TOYOPEARL GigaCap DEAE-650 (manufactured by TOSOH), Cellufine MAX Q-r (manufactured by JNC), Cellufine MAX Q-h (manufactured by JNC) and Cellufine MAX DEAE (manufactured by JNC), and is not restricted thereto.

A cation exchange resin usable in a cation exchange chromatography is not restricted as long as the cation exchange resin exhibits a cation exchanging action. A cation exchange resin is exemplified by Capto S (manufactured by GE Healthcare Life Sciences), Capto SP ImpRes (manufactured by GE Healthcare Life Sciences), SP Sepharose High Performance (manufactured by GE Healthcare Life Sciences), RESOURCE S (manufactured by GE Healthcare Life Sciences), SOURCE 30S (manufactured by GE Healthcare Life Sciences), YMC BioPro S (manufactured by YMC), YMC BioPro CM (manufactured by YMC), TOYOPEARL SP-650 (manufactured by TOSOH), TOYOPEARL GigaCap 5-650 (manufactured by TOSOH), TOYOPEARL CM-650 (manufactured by TOSOH), TOYOPEARL GigaCap CM-650 (manufactured by TOSOH), Cellufine MAX S-r (manufactured by JNC), Cellufine MAX S-h (manufactured by JNC) and Cellufine MAX CM (manufactured by JNC), and is not restricted thereto.

A hydrophobic chromatography resin usable in a hydrophobic chromatography is not restricted as long as the hydrophobic chromatography resin exhibits a hydrophobic interaction. A hydrophobic chromatography resin is exemplified by Phenyl Sepharose High Performance (manufactured by GE Healthcare Life Sciences), Buthyl Sepharose High Performance (manufactured by GE Healthcare Life Sciences), Phenyl Sepharose 6 Fast Flow (manufactured by GE Healthcare Life Sciences), Buthyl Sepharose 6 Fast Flow (manufactured by GE Healthcare Life Sciences), Octyl Sepharose 4 Fast Flow (manufactured by GE Healthcare Life Sciences), Buthyl Sepharose 4 Fast Flow (manufactured by GE Healthcare Life Sciences), Macro-Prep HIC (manufactured by Bio-Rad Laboratories), TOYOPEARL Ethyl-650 (manufactured by TOSOH), TOYOPEARL PPG-650 (manufactured by TOSOH), TOYOPEARL Phenyl-650 (manufactured by TOSOH), TOYOPEARL Buthyl-650 (manufactured by TOSOH), Cellufine MAX Phenyl (manufactured by JNC), Cellufine MAX Buthyl (manufactured by JNC) and Cellufine MAX Phenyl LS (manufactured by JNC), and is not restricted thereto.

A hydroxyapatite resin usable in a hydroxyapatite chromatography is exemplified by Ceramic Hydroxyapatite (manufactured by Bio-Rad Laboratories), Ceramic Fluoloapatite (manufactured by Bio-Rad Laboratories), MPC Ceramic HydroxyFluoloapatite (manufactured by Bio-Rad Laboratories) and HA Ultrogel (manufactured by PALL), and is not restricted thereto.

A resin usable in a mix mode chromatography is not restricted as long as the resin is a mixture of 2 or more resins which have different interactions. A resin usable in a mix mode chromatography is exemplified by Capto MMC (manufactured by GE Healthcare Life Sciences), Capto Adhere (manufactured by GE Healthcare Life Sciences) and Eshumuno HCX (manufactured by Merck Millipore), and is not restricted thereto.

A resin usable in an affinity chromatography is not restricted as long as the resin has an affinity for a target substance to be adsorbed. A resin usable in an affinity chromatography is exemplified by KANEKA KanCapA (manufactured by KANEKA), KANEKA KanCapA 3G (manufactured by KANEKA), KANEKA KanCapG (manufactured by KANEKA), KANEKA KanCapL (manufactured by KANEKA), MabSelect (manufactured by GE Healthcare Life Sciences), MabSelect Xtra (manufactured by GE Healthcare Life Sciences), MabSelect SuRe (manufactured by GE Healthcare Life Sciences), MabSelect SuRe LX (manufactured by GE Healthcare Life Sciences), MabSelect SuRe pcc (manufactured by GE Healthcare Life Sciences), MabSelect PrismA (manufactured by GE Healthcare Life Sciences), Protein G Sepharose 4 Fast Flow (manufactured by GE Healthcare Life Sciences), KappaSelect (manufactured by GE Healthcare Life Sciences), LamdaFabSelect (manufactured by GE Healthcare Life Sciences), Capto L (manufactured by GE Healthcare Life Sciences), Glutathione Sepharose 4 Fast Flow (manufactured by GE Healthcare Life Sciences), GSTrap 4B (manufactured by GE Healthcare Life Sciences), Glutathione Sepharose 4B (manufactured by GE Healthcare Life Sciences), IgG Sepharose 6 Fast Flow (manufactured by GE Healthcare Life Sciences), TOYOPEARL AF-rProteinA-650F (manufactured by TOSOH), TOYOPEARL AF-rProteinA-HC650F (manufactured by TOSOH), TOYOPEARL AF-rProteinL-650F (manufactured by TOSOH), TOYOPEARL AF-Red-650M (manufactured by TOSOH), TOYOPEARL AF-Chelate-650M (manufactured by TOSOH) and Amsphere A3 (manufactured by JSR Life Sciences), and is not restricted thereto.

After the antibody or antibody-like molecule is purified, the antibody or antibody-like molecule may be concentrated by reducing an amount of a solvent, or a solvent may be exchanged.

An amount of an impurity can be determined in any stages by a commercially available assay kit in addition to absorbance analysis, electrophoresis, HPLC or the like. For example, an amount of a protein derived from a host CHO cell can be determined by using CHO HCP ELISA kit (manufactured by Cygnus). When there is not a commercially available assay kit for a target contaminating protein, a desired detection system can be prepared by immunizing an animal such as a chicken with the contaminating protein. An amount of an impurity such as DNA can be determined by qPCR or the like.

The present application claims the benefit of the priority dates of Japanese patent application No. 2018-163228 filed on Aug. 31, 2018. All of the contents of the Japanese patent application No. 2018-163228 filed on Aug. 31, 2018, are incorporated by reference herein.

EXAMPLES

Hereinafter, the examples are described to demonstrate the present invention more specifically, but the present invention is in no way restricted by the examples, and the examples can be appropriately modified to be carried out within a range which adapts to the contents of this specification. Such a modified example is also included in the range of the present invention. Commercially available reagents are used in the Examples unless otherwise stated.

Example 1: Treatment of Culture Fluid of Animal Cell Using Basic Magnesium Carbonate Basic magnesium carbonate was added and dispersed in a buffer (pH 7.0) containing 0.025 mol/mL sodium phosphate in a concentration of 10 wt % to prepare a basic magnesium carbonate suspension. An animal cell culture fluid containing the same amount of monoclonal antibody (IgG) was added to the basic magnesium carbonate suspension, and the mixture was stirred well and then left to stand in an incubator at 25° C. for 1 hour. Next, the treated solution was centrifuged at 15,000 rpm at 15° C. for 10 minutes, and only a supernatant was recovered.

Comparative Example 1: Treatment of CHO Culture Fluid Using Poly(Diallyldimethylammonium Chloride)

A similar procedure to Example 1 was performed except that 0.01% of poly(diallyldimethylammonium chloride) (pDACMAC) as a publicly known flocculant was added in place of basic magnesium carbonate.

Test Example 1: Measurement of Antibody Concentration and Content Amounts of DNA and Host Cell Protein (HCP)

A concentration of IgG and content amounts of DNA and a host cell protein, i.e. HCP, were determined in the culture supernatant before the treatment and solutions of Example 1 and Comparative example 1 by the following procedures.

The IgG concentration was determined by Protein A chromatography. A Protein A affinity column TSKgel SuperSW mAb manufactured by TOSOH was connected to a chromatography system AKTA explorer 10S manufactured by GE Healthcare. A buffer (pH 6.7) containing 0.02 mol/mL sodium phosphate and 0.01 mol/mL sodium sulfate was passed through the column at room temperature in a flow rate of 0.7 ml/min, and 50 µL of a sample to be assessed was injected thereto. After 5 Column Volume (CV) of a buffer (pH 6.7) containing 0.02 mol/mL sodium phosphate and 0.01 mol/mL sodium sulfate was sent as a washing liquid, 10 CV of a buffer (pH 2.5) containing 0.02 mol/mL sodium phosphate was sent as an eluent. UV absorbance at 280 nm of an elution peak was measured using a UV absorption spectrometer attached to the system.

A content amount of HCP was measured using CHO Host Cell Protein ELISA Kit, 3rd Generation manufactured by *Cygnus* in accordance with an accompanying protocol.

A content amount of DNA was measured using CHO DNA Amplification Kit in Tubes manufactured by *Cygnus* in accordance with an accompanying protocol.

HCP amounts before and after the treatment are shown in FIG. 1 and Table 1.

TABLE 1

| | Additive | IgG conc. (mg/mL) | HCP conc. (ng/ml) | DNA conc. (ng/ml) |
|---|---|---|---|---|
| Control | No additive | 0.67 | 74,500 | 54,166 |
| Example 1 | Basic magnesium carbonate | 0.65 | 31,728 | 73 |
| Comparative example 1 | p-DACMAC | 0.68 | 78,506 | 12,208 |

As the results shown in Table 1 and FIG. 1, it was clear that HCP as an impurity can be effectively reduced while the target IgG remains in a solution by adding basic magnesium carbonate. Thus, it was demonstrated that an impurity can be reduced by treating the aqueous solution and suspension containing the antibody or antibody-like molecule and an impurity.

Example 2: Effect Assessment of Additive Amount of Basic Magnesium Carbonate on Impurity Protein Removal Rate Basic magnesium carbonate was added to a culture supernatant of an animal cell containing a monoclonal antibody in concentrations of 1 w/v %, 5 w/v % or 10 w/v %. The mixture was stirred using Mix Rotor at room temperature for 18 hours, and then centrifuged at 15,000 rpm for 5 minutes to obtain a supernatant as a treated liquid. Concentrations of IgG, HCP and DNA were determined. The result is shown in Table 2, FIG. 2 and FIG. 3.

TABLE 2

| Additive amount of basic magnesium carbonate (w/v %) | IgG conc. (mg/mL) | HCP conc. (ng/ml) | DNA conc. (ng/ml) |
|---|---|---|---|
| No addition | 1.34 | 283,333 | 5,850 |
| 1% | 1.34 | 169,240 | 1 |
| 5% | 1.33 | 140,998 | 49 |
| 10% | 1.31 | 100,843 | 10 |

As the result of the assessment, when an additive amount of basic magnesium carbonate was larger in the range of 1 to 10 w/v %, HCP concentration was lower. It was found that there is not a difference in DNA concentrations and an addition of 1 w/v % has a sufficient capacity to remove an impurity.

Example 3: Effect of Water-Insoluble Inorganic Compound on Removal of Impurity and Combination Effect with Activated Carbon To a culture supernatant of an animal cell containing a monoclonal antibody, 1 wt % of the water-insoluble inorganic compound and 0.67 wt % of an activated carbon were respectively added. The mixture was stirred using Mix Rotor at room temperature for 18 hours, and then centrifuged at 15,000 rpm for 5 minutes to obtain a supernatant as a treated liquid. As the water-insoluble inorganic compound, basic magnesium carbonate, magnesium oxide, magnesium hydroxide, calcium sulfate or aluminum oxide were used. A concentration of IgG and content amounts of HCP and DNA were determined. The result is shown in Table 3, FIG. 4 and FIG. 5.

TABLE 3

| Water-insoluble inorganic compound/activated carbon | IgG conc. (mg/mL) | HCP conc. (ng/ml) | DNA conc. (ng/ml) |
| --- | --- | --- | --- |
| no addition/without | 1.34 | 283,396 | 13,708 |
| MgCO$_3$ (basic)/without | 1.31 | 190,251 | 4 |
| MgCO$_3$ (basic)/with | 1.18 | 45,754 | 5 |
| Al$_2$O$_3$/without | 1.36 | 284,481 | 9,681 |
| Al$_2$O$_3$/with | 1.19 | 89,869 | 5,473 |
| MgO/without | 1.33 | 226,200 | 1,183 |
| MgO/with | 1.21 | 40,829 | 3 |
| Mg(OH)$_2$/without | 1.30 | 204,732 | 2,297 |
| Mg(OH)$_2$/with | 1.19 | 35,612 | 2,055 |
| CaSO$_4$/without | 1.32 | 244,579 | 11,623 |
| CaSO$_4$/with | 1.18 | 49,322 | 7,561 |
| MgSO$_4$/without | 1.33 | 270,643 | 13,294 |
| MgSO$_4$/with | 1.18 | 79,429 | 12,330 |
| MgCl$_2$/without | 1.35 | 284,801 | 14,260 |
| MgCl$_2$/with | 1.16 | 100,755 | 13,427 |
| no addition/with | 1.18 | 104,737 | 12,003 |

As the result of the assessment, not only basic magnesium carbonate but also magnesium oxide, magnesium hydroxide, calcium sulfate and aluminum oxide as the water-insoluble inorganic compound have an effect to remove an impurity protein. All of the compounds are preferably used for producing a bio pharmaceutical product, since the compounds are inorganic compounds used in a pharmaceutical product and for medical use. It was found that when the water-insoluble inorganic compound is combined with an activated carbon, a recovery rate of IgG is decreased by about 10% but an effect on a removal of an impurity is further improved.

Example 4: Improvement of Capturing Step Using Protein a by Treatment with Addition of Basic Magnesium Carbonate To a culture supernatant of an animal cell containing a monoclonal antibody, 1 wt % of basic magnesium carbonate was added. The mixture was stirred using Mix Rotor at room temperature for 18 hours, and then centrifuged at 15,000 rpm for 5 minutes and filtrated using a filter to obtain a supernatant. The supernatant was loaded on a column filled with rProtein A carrier for producing monoclonal antibody drug ("Mabselect SuRe LX" manufactured by GE Healthcare Life Sciences) (1 mL) or high performance carrier for Protein A chromatography ("KENEKA KanCapA 3G prepacked column" manufactured by KENEKA) (1 mL), and eluted using 50 mM citrate buffer. Then the column was washed using 0.1 M NaOH. The IgG, HCP and DNA in the obtained loaded liquid, eluted liquid and washing liquid were measured. The result is shown in Table 4, FIG. 6, FIG. 7 and FIG. 8.

TABLE 4

| | Eluted liquid | | | Washing liquid | |
| --- | --- | --- | --- | --- | --- |
| Column/ MgCO$_3$ addition | IgG recovery rate (%) | HCP conc. (ppm) | DNA conc. (ppm) | HCP conc. (ng/mL) | DNA conc. (ng/mL) |
| SuRe LX/without | 92 | 70 | 0.07 | 314.5 | 56.2 |
| SuRe LX/with | 89 | 25 | 0.00 | 11.2 | 4.4 |
| KanCapA 3G/without | 92 | 38 | 0.03 | 238.0 | 51.5 |
| KanCapA 3G/with | 90 | 17 | 0.00 | 19.7 | 0.4 |

As the result of the assessment, it was found that an accumulation of an impurity on a Protein A carrier can be suppressed and a quality of an eluted antibody liquid can be improved.

Example 5: Removal of Impurity by Column Filled with Basic Magnesium Carbonate A chromatography column having a volume of 1 mL was filled with basic magnesium carbonate. A culture supernatant of an animal cell containing a monoclonal antibody was passed through the column, and content amounts of IgG, HCP and DNA were determined. The result is shown in Table 5, FIG. 9 and FIG. 10.

TABLE 5

| Basic magnesium carbonate column | IgG conc. (mg/mL) | HCP conc. (ng/ml) | DNA conc. (ng/ml) |
| --- | --- | --- | --- |
| Before passing liquid | 1.33 | 288,861 | 11,285 |
| After passing liquid | 1.34 | 209,439 | 184 |

As the result of the assessment, it was found that an impurity such as HCP and DNA can be also reduced by using a column filled with basic magnesium carbonate.

Example 6: Removal of Impurity from VHH-Containing Culture Supernatant Derived from *Pichia* by Basic Magnesium Carbonate To a *Pichia* culture supernatant containing a heavy chain antibody (VHH), 0.67 wt % of an activated carbon and/or 1 wt % of basic magnesium carbonate was added. The mixture was stirred using Mix Rotor for 2 hours, and then centrifuged at 15,000 rpm for 5 minutes to obtain only a supernatant as a treated liquid. The culture fluid before the treatment and the treated liquid were analyzed by SDS-PAGE. A VHH recovery rate and a rate of residual impurity were determined by scanning strengths of the band of the target VHH around 15 kDa and the band of an impurity around 18 and 25 kDa in the obtained SDS-PAGE. The obtained result is shown in Table 6.

TABLE 6

| Basic magnesium carbonate/ activated carbon | VHH recovery rate | Rate of residual impurity (18 kD) | Rate of residual impurity (25 kD) |
| --- | --- | --- | --- |
| Addition/without | 97% | 50% | 79% |
| No addition/with | 94% | 30% | 17% |
| Addition/with | 92% | 24% | 14% |

As the result of the assessment, it was found that basic magnesium carbonate also has an effect on a removal of an impurity from *Pichia* culture supernatant containing VHH, and exhibits further high effect on a removal of an impurity by combining with an activated carbon.

Example 7: Removal of Impurity from *Pichia* Culture Supernatant Containing scFV by Basic Magnesium Carbonate To a *Pichia* culture supernatant containing a single-chain antibody (scFV), 0.67 wt % of an activated carbon and/or 1 wt % or 10 wt % of basic magnesium carbonate was added. The mixture was stirred using Mix Rotor for 2 hours, and then centrifuged at 15,000 rpm for 5 minutes to recover a supernatant as a treated liquid. The culture fluid before the treatment and the treated liquid were analyzed by SDS-PAGE. A VHH recovery rate and a rate of residual impurity were determined by scanning strengths of the band of the target scFV around 30 kDa and the other bands of an impurity in the obtained SDS-PAGE. The obtained result is shown in Table 7.

TABLE 7

| Basic magnesium carbonate/ activated carbon | scFV recovery rate | Rate of residual impurity |
| --- | --- | --- |
| 1 wt % addition/without | 103% | 84% |
| 10 wt % addition/ without | 87% | 40% |
| No addition/with | 67% | 63% |
| 1 wt % addition/with | 87% | 57% |
| 10 wt % addition/with | 68% | 26% |

As the result of the assessment, it was found that basic magnesium carbonate also has an effect on a removal of an impurity from *Pichia* culture supernatant containing scFV, and when basic magnesium carbonate is combined with an activated carbon, a yield is somewhat decreased but basic magnesium carbonate exhibits further high effect on a removal of an impurity.

Example 8: Removal of Impurity from *Escherichia coli* Culture Supernatant Containing VHH by Basic Magnesium Carbonate To a *Escherichia coli* culture supernatant containing VHH, 1 wt % or 10 wt % of basic magnesium carbonate was added. The mixture was stirred using Mix Rotor for 2 hours, and then centrifuged at 15,000 rpm for 5 minutes to recover a supernatant as a treated liquid. The culture fluid before the treatment and the treated liquid were analyzed by SDS-PAGE. A VHH recovery rate and a rate of residual impurity were determined by scanning strengths of the band of the target scFV around 30 kDa and the other bands of an impurity in the obtained SDS-PAGE. The obtained result is shown in Table 8.

TABLE 8

| Amount of added basic magnesium carbonate (w/v %) | scFV recovery rate | Rate of residual impurity |
| --- | --- | --- |
| 0 | 100% | 100% |
| 1 | 91% | 85% |
| 10 | 69% | 21% |

As the result of the assessment, it was found that basic magnesium carbonate also has an effect on a removal of an impurity from *Pichia* culture supernatant containing scFV.

Example 9: Removal of Impurity from Fab-Containing Culture Fluid by Basic Magnesium Carbonate To a CHO culture supernatant containing Fab, 0 wt %, 1 wt % or 10 wt % of basic magnesium carbonate was added. The mixture was stirred using Mix Rotor for 2 hours, and then centrifuged at 15,000 rpm for 5 minutes to recover a supernatant as a treated liquid. Concentrations of Fab, HCP and DNA in the treated liquid were measured. The concentration of Fab was measured by Protein G chromatography.

TABLE 9

| Amount of added basic magnesium carbonate (w/v %) | Fab conc. (mg/mL) | HCP conc. (ng/ml) | DNA conc. (ng/ml) |
| --- | --- | --- | --- |
| 0 | 0.2 | 166,503 | 9825 |
| 1 | 0.2 | 121,307 | 94 |
| 10 | 0.2 | 67,829 | 23 |

As the result of the assessment, it was found that basic magnesium carbonate also has an effect on a removal of an impurity from CHO culture supernatant containing Fab.

Example 10: Removal of Aggregate from Antibody-Containing Culture Fluid by Basic Magnesium Carbonate To a CHO culture supernatant containing a monoclonal antibody, 0 wt % or 1 wt % of basic magnesium carbonate was added. The mixture was stirred using Mix Rotor for 18 hours, and then centrifuged at 15,000 rpm for 5 minutes to recover a supernatant as a treated liquid. A concentration of IgG and a content amount of an aggregate in the treated liquid were measured. The content amount of the aggregate was measured by gel filtration chromatography.

TABLE 10

| Amount of added basic magnesium carbonate (w/v %) | IgG conc. (mg/mL) | Aggregate (%) |
| --- | --- | --- |
| 0 | 3.5 | 1.1 |
| 1 | 3.5 | 0.4 |

As the result of the assessment, it was found that basic magnesium carbonate has an effect on a removal of an aggregate.

Example 11: Removal of Impurity by Combination of Basic Magnesium Carbonate and Endonuclease To a CHO culture supernatant containing a monoclonal antibody, 1 wt % of basic magnesium carbonate and/or 100

U/mL of KANEKA endonuclease was added. The mixture was stirred using Mix Rotor for 18 hours, and then centrifuged at 15,000 rpm for 5 minutes to recover a supernatant as a treated liquid. Concentration of IgG, HCP and DNA in the treated liquid were measured.

TABLE 11

| basic magnesium carbonate/ endonuclease | IgG conc. (mg/mL) | HCP conc. (ng/ml) | DNA conc. (ng/ml) |
|---|---|---|---|
| without/without | 1.3 | 164,420 | 22,248 |
| with/without | 1.3 | 136,323 | 11 |
| without/with | 1.3 | 166,454 | 5 |
| with/with | 1.3 | 125,187 | 2 |

As the result of the assessment, it was found that the capacity to remove an impurity can be further improved by combining basic magnesium carbonate and an endonuclease.

Example 12: Removal of Impurity by Trimagnesium Phosphate

To an animal cell culture supernatant containing a monoclonal antibody, 1 wt % or 10 wt % of trimagnesium phosphate and 0.67 wt % of an activated carbon were respectively added. The mixture was stirred using Mix Rotor at room temperature for 18 hours, and then centrifuged at 15,000 rpm for 5 minutes to recover a supernatant as a treated liquid. Concentrations of IgG, HCP and DNA in the treated liquid were measured. The result is shown in Table 12.

TABLE 12

| $Mg_3(PO_4)_2$/ activated carbon | IgG conc. (mg/mL) | HCP conc. (ng/mL) | DNA conc. (ng/mL) |
|---|---|---|---|
| No addition/without | 3.5 | 194,547 | 1 |
| 1 w % addition/without | 3.4 | 185,416 | 0 |
| 10 w % addition/without | 3.5 | 180,325 | 0 |
| No addition/with | 3 | 30,006 | 0.865 |
| 1 w % addition/with | 3.1 | 21,837 | 0.021 |
| 10 w % addition/with | 3 | 14,185 | 0.014 |

As the result of the assessment, it was found that trimagnesium phosphate also has the capacity to remove an impurity, and the capacity to remove an impurity can be further improved in combination with an activated carbon.

The invention claimed is:

1. A method for purifying an antibody or a protein, the method comprising the step of:
adding a pre-formed water-insoluble inorganic compound to an aqueous solution or a suspension comprising the antibody or the protein and an impurity or filling a column with a pre-formed water-insoluble inorganic compound and passing an aqueous solution or a suspension comprising the antibody or the protein through the column to adsorb the impurity onto said pre-formed water-insoluble inorganic compound and obtain a liquid part comprising the antibody or the protein,
wherein said pre-formed water-insoluble inorganic compound comprises at least one member selected from the group consisting of magnesium carbonate, magnesium oxide, magnesium phosphate, and aluminum oxide, and the antibody or the protein is at least one member selected from the group consisting of polyclonal antibody, monoclonal antibody, human antibody, humanized antibody, chimeric antibody, single-chain antibody, heavy chain antibody, multivalent antibody, Fab, F(ab'), F(ab')$_2$, Fc, Fc fusion protein, bispecific antibody, heavy chain, light chain, single-chain Fv, sc(Fv)$_2$, disulfide bonded Fv, Diabody or micro-antibody.

2. The method according to claim 1, further comprising a step of contacting the aqueous solution or the suspension with an activated carbon.

3. The method according to claim 1, wherein the aqueous solution or the suspension is a culture fluid comprising the antibody or the protein.

4. The method according to claim 1, wherein the aqueous solution or the suspension is a culture supernatant obtained by a centrifugation treatment or a membrane treatment of a culture fluid.

5. The method according to claim 3, wherein the culture fluid is a culture fluid for a recombinant host cell to produce the antibody or the protein.

6. The method according to claim 1, wherein the aqueous solution or the suspension is a homogenate or an extract of a recombinant host cell.

7. The method according to claim 1, wherein the aqueous solution or the suspension is a supernatant obtained by subjecting a homogenate or an extract of a recombinant host cell to a centrifugation treatment or a membrane treatment.

8. The method according to claim 1, wherein the aqueous solution or the suspension is an extract derived from a living body.

9. The method according to claim 1, wherein the antibody or the protein is an Fc-containing protein.

10. The method according to claim 1, wherein the antibody or the protein is a low molecular weight antibody selected from the group consisting of Fab, F(ab'), F(ab')$_2$, Fc, heavy chain, light chain, single-chain Fv(scFv), sc(Fv)$_2$, disulfide bonded Fv, single-chain antibody, heavy chain antibody, multivalent antibody, bispecific antibody, Diabody and micro-antibody.

11. The method according to claim 1, further comprising a step of treating the aqueous solution or the suspension with a flocculant.

12. The method according to claim 1, further comprising a step of treating the aqueous solution or the suspension with an endonuclease.

13. The method according to claim 1, further comprising a step of subjecting the antibody or the protein in the liquid part to a column treatment or a membrane filtration treatment.

14. The method according to claim 1, comprising a separating step for separating said pre-formed water-insoluble inorganic compound having impurity adsorbed thereon from said aqueous solution or suspension which involves centrifugation and/or filtration.

15. The method according to claim 1, wherein the aqueous solution or the aqueous suspension is mixed with said pre-formed water-insoluble inorganic compound to absorb impurity on said inorganic compound.

16. The method of claim 15, comprising a separating step which comprises separating the inorganic compound having impurity adsorbed thereon from the aqueous solution containing purified antibody or protein.

17. The method according to claim 16, wherein the aqueous solution or the aqueous suspension is passed through a column containing said pre-formed water-insoluble inorganic compound to absorb impurity on said inorganic compound in said column and said separating step comprises recovering the purified antibody or protein having a reduced level of impurity from the column.

18. The method according to claim 1, wherein an average particle diameter of the pre-formed water-insoluble inorganic compound is 0.1 μm or more and 1000 μm or less.

19. The method according to claim 1, wherein the pre-formed water-insoluble inorganic compound is basic magnesium carbonate.

20. The method according to claim 1, wherein said antibody or protein is at least one member selected from the group consisting of an IgG antibody, protein A, a variable domain heavy chain antibody, scFV and Fab.

* * * * *